(12) United States Patent
Evans et al.

(10) Patent No.: US 10,874,732 B2
(45) Date of Patent: Dec. 29, 2020

(54) THERMALLY STABLE ROTAVIRUS VACCINE FORMULATIONS AND METHODS OF USE THEREOF

(71) Applicant: Merck Sharp & Dohme Corp., Rahway, NJ (US)

(72) Inventors: Robert K. Evans, Bangor, MA (US); Erica L. Strable, Gilbertsville, PA (US); Lynne Isopi, Sellersville, PA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/062,754

(22) PCT Filed: Dec. 13, 2016

(86) PCT No.: PCT/US2016/066248
§ 371 (c)(1),
(2) Date: Jun. 15, 2018

(87) PCT Pub. No.: WO2017/106115
PCT Pub. Date: Jun. 22, 2017

(65) Prior Publication Data
US 2019/0000957 A1    Jan. 3, 2019

Related U.S. Application Data

(60) Provisional application No. 62/269,419, filed on Dec. 18, 2015.

(51) Int. Cl.
| | | |
|---|---|---|
| A61K 39/12 | (2006.01) | |
| A61P 31/14 | (2006.01) | |
| A61K 9/00 | (2006.01) | |
| A61K 39/00 | (2006.01) | |

(52) U.S. Cl.
CPC .............. *A61K 39/12* (2013.01); *A61K 9/006* (2013.01); *A61K 39/0016* (2013.01); *A61P 31/14* (2018.01); *A61K 2039/5254* (2013.01); *A61K 2039/542* (2013.01); *A61K 2039/6037* (2013.01); *A61K 2039/70* (2013.01); *C12N 2720/12334* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,932,223 A | 8/1999 | Burke et al. | |
| 6,616,931 B1 * | 9/2003 | Burke | A61K 39/15 424/215.1 |
| 6,656,719 B1 | 12/2003 | Gould et al. | |
| 8,192,747 B2 * | 6/2012 | Vande Velde | A61K 39/15 424/215.1 |
| 2012/0237547 A1 * | 9/2012 | Vande Velde | A61K 39/15 424/215.1 |

FOREIGN PATENT DOCUMENTS

| | | |
|---|---|---|
| WO | 1998013065 A1 | 4/1998 |
| WO | 2006087205 A1 | 8/2006 |
| WO | 2009042202 A2 | 4/2009 |
| WO | 2013029033 A2 | 2/2013 |
| WO | 2018041891 A1 | 3/2018 |

OTHER PUBLICATIONS

Giaquinto, Carlo et al., Summary of effectiveness and impact of rotavirus vaccination with the oral pentavalent rotavirus vaccine, Human Vaccines, 2011, 734-748, 7.
Patel, Manish M. et al., Removing the Age Restrictions for Rotavirus Vaccination: A Benefit-Risk Modeling Analysis, PLoS Medicine, 2012, 1-10, 9(10).
Weiss, S. et al., Rapid Inactivation of Rotaviruses by Exposure to Acid Buffer or Acidic Gastric Juice, Journal of General Virology, 1985, 2725-2730, 66.
World Health Organization, WHO-UNICEF policy statement on the use of vaccine vial monitors in immunization services, WHO-UNICEF, 1999, 1-4, WHOV&B/99.18.
World Health Organization, Technical Review of Vaccine Vial Monitor Implementation, World Health Organization-Rotavirus Vaccines, 2002, 1-47, VVM.
World Health Organization, Weekly epidemiological record Relevééepidémiologique hebdomadaire, WHO Weekly Epidemiological Record, 2013, 49-64, 88.

(Continued)

*Primary Examiner* — Shanon A. Foley
*Assistant Examiner* — Myron G Hill
(74) *Attorney, Agent, or Firm* — David Van Goor; Anna L. Cocuzzo

(57) ABSTRACT

The present invention relates to thermally stable oral rotavirus vaccine formulations comprising one or more rotavirus reassortant or attenuated rotavirus strains, a pharmaceutically acceptable calcium salt, adipic acid, sucrose, and sodium phosphate, wherein each of the one or more rotavirus reassortant or attenuated rotavirus strain is stable for 7 days at 37° C., for 45 days at 25° C. and for 2 years or more at 2-8° C. The calcium containing formulations of the invention may further comprise one or more excipients which are present in an amount that is effective to optimize the calcium ions free in solution to stabilize the rotavirus particles. In embodiments of the invention, the formulation comprises a surfactant, such as polysorbate 80. The invention also relates to methods of using the rotavirus vaccine compositions of the invention to prevent rotavirus infection, or to reduce the likelihood of infection or to prevent, ameliorate, or delay the onset or progression of the clinical manifestations thereof.

17 Claims, 3 Drawing Sheets

(56) References Cited

OTHER PUBLICATIONS

Clark, H. Fred, Safety, immunogenicity and efficacy in healthy infants of G1 and G2 human reassortant rotavirus vaccine in a new stabilizer/buffer liquid formulation, Pediatric Infectious Disease Journal, 2003, 914-920, vol. 22, No. 10.
European Medicines Agency, Science Medicines Health, Assessment report for paediatric studies submitted according to Article 46 of the Regulation (EC) No. 1901/2006, Procedure Management and Committees Support Division, 2016, 1-9, EMA/CHMP/108077/2016.
Goveia, Michelle G., Development, clinical evaluation, and post-licensure impact of RotaTeq, a pentavalent rotavirus vaccine, Annals of the New York Academy of Sciences, 2011, 14-18, vol. 1222, No. 1.
Martinon-Torres, Federico, Safety, Tolerability and Immunogenicity of Pentavalent Rotavirus Vaccine Manufactured by a Modified Process, Pediatric Infectious Disease Journal, 2017, 417-422, vol. 36, No. 4.
Retrieved from Internet: URL:https://www.ema.europa.eu/en/documents/scientific-discussion/rotateq-epar-scientific-discussion_en.pdf [retrieved on Jul. 8, 2019].
Retrieved from the Internet: URL:https://clinicaltrials.gov/ct2/history/NCT016000092?V 15=View#StudyPageTop [retrieved on Jul. 8, 2019].
Retrieved from the Internet: URL:https://ec.europa.ei/health/documents/community-register/2015/20150408131614/anx_131614_en.pdf [retrieved on Jul. 8, 2019].
Retrieved from the Internet: URL:https://www.impfkritik.de/upload/pdf/fachinfo/RotaTeq-Merck-USA-2007-09.pfd [retrieved on Jul. 8, 2019].
Retrieved from the Internet: URL:https://www.unicef.org/supply/files/Temperature_Monitoring_Devices.pdf [retrieved on Jul. 4, 2019].

\* cited by examiner

Calcium Precipitation at 37°C

| pH | Calcium Concentration | Day 0 | Day 3 | Day 7 | Day 14 | Day 18 | Day 39 |
|---|---|---|---|---|---|---|---|
| 6.2 | 3.0 mM | Clear | Clear | Clear | Clear | Clear | Clear |
| | 3.15 mM | Clear | Clear | Clear | Clear | Clear | Clear |
| | 3.25 mM | Clear | Clear | Clear | Clear | Clear | Clear |
| | 3.3 mM | Clear | Clear | Clear | Clear | Clear | Clear |
| | 3.5 mM | Clear | Clear | Clear | Clear | Clear | Clear |
| | 3.75 mM | Clear | Clear | Clear | Clear | Clear | Clear |
| | 4.0 mM | Clear | Clear | PPT | PPT | PPT | PPT |
| 6.4 | 3.0 mM | Clear | Clear | Clear | Clear | Clear | Clear |
| | 3.15 mM | Clear | Clear | Clear | Clear | Clear | Clear |
| | 3.25 mM | Clear | Clear | Clear | Clear | Clear | Clear |
| | 3.3 mM | Clear | Clear | Clear | Clear | Clear | Clear |
| | 3.5 mM | Clear | Clear | Clear | Clear | Clear | Clear |
| | 3.75 mM | Clear | Clear | Clear | Clear | Clear | Clear |
| | 4.0 mM | Clear | Clear | PPT | PPT | PPT | PPT |
| 6.7 | 3.0 mM | Clear | Clear | Clear | Clear | Clear | Clear |
| | 3.15 mM | Clear | Clear | Clear | Clear | Clear | Clear |
| | 3.25 mM | Clear | Clear | Clear | Clear | Clear | Clear |
| | 3.3 mM | Clear | Clear | Clear | Clear | Clear | Clear |
| | 3.5 mM | Clear | Clear | Clear | Clear | Clear | Clear |
| | 3.75 mM | Clear | Clear | PPT | PPT | PPT | PPT |
| | 4.0 mM | Clear | Clear | PPT | PPT | PPT | PPT |

Statistical Analysis of Noninferiority of GMT for the SNA Responses to Reassortants Rotavirus Serotypes G1, G2, G3, G4 and P1A (Per-Protocol Population)

| Antigen | RotaTeq™ New Formulation (N=510) | | RotaTeq™ Current Formulation (N=504) | | Ratio of GMTs†§ (95% CI)‡ | P-value | Similarity Conclusion |
|---|---|---|---|---|---|---|---|
| | n | Estimated GTM† | n | Estimated GTM† | | | |
| Serotypes G1 | 495 | 99.5 | 488 | 107.6 | 0.92 (0.79, 1.07) | <0.001 | Similar‡ |
| Serotypes G2 | 495 | 30.7 | 488 | 26.7 | 1.15 (0.99, 1.33) | <0.001 | Similar‡ |
| Serotypes G3 | 495 | 82.6 | 488 | 25.8 | 3.20 (2.75, 3.74) | <0.001 | Similar‡ |
| Serotypes G4 | 495 | 77.3 | 488 | 72.8 | 1.06 (0.94, 1.20) | <0.001 | Similar‡ |
| Serotypes P1A | 495 | 107.2 | 488 | 92.5 | 1.16 (1.00, 1.35) | <0.001 | Similar‡ |

† GMTs and their ratio were based on a model with terms for treatment and country, with the constraint that the mean baseline is the same for all treatment groups.
‡ A 95% CI on the ratio excluding a 1.5 fold decrease or more (i.e., the lower bound of CI > 0.67) and associated 1-sided p-value ≤ 0.025 implies that the difference is statistically significantly less than the pre-specified clinically relevant decrease of 1.5-fold and allows for a conclusion of non-inferiority.
§ [New Formulation group]/[Current Formulation group].
SNA = Serum neutralization assay.
N = Number of subjects vaccinated.
n = Number of subjects contributing to the per-protocol analyses.
CI = Confidence interval.

Immunogenicity Summary for Serum Anti-rotavirus IgA
(Per-Protocol Population)

| Antigen (Assay) | Parameter | RotaTeq™ New Formulation (N=510) | | | RotaTeq™ Current Formulation (N=504) | | |
|---|---|---|---|---|---|---|---|
| | | n | Observed Response. | 95% CI | n | Observed Response. | 95% CI |
| Serum Anti-rotavirus IgA | Predose 1 GMT | 490 | 0.2 | (0.1, 0.2) | 484 | 0.2 | (0.2, 0.2) |
| | Postdose 3 GMT | 474 | 240.5 | (210.4, 274.8) | 474 | 235.5 | (204.1, 271.8) |
| | Proportion of subjects with a ≥ 3-fold rise | 475 | 97.3% (462/475) | (95.4%, 98.5%) | 477 | 95.2% (454/477) | (92.9%, 96.9%) |

N = Number of subjects vaccinated.
n = Number of subjects contributing to the per-protocol analyses. (for ≥ 3 fold rise, limited to per-protocol subjects with both predose 1 and prodose 3 serology).
GMT = Geometric mean titer.
CI = Confidence interval.

FIG.3

THERMALLY STABLE ROTAVIRUS VACCINE FORMULATIONS AND METHODS OF USE THEREOF

FIELD OF THE INVENTION

The invention relates to thermally stable rotavirus vaccine formulations that elicit an immunological response against rotavirus, useful for the prevention and/or treatment of rotavirus infection in a subject, and/or the clinical manifestations thereof.

CROSS-REFERENCE TO RELATED APPLICATIONS

This application is a U.S. National Phase application of International Patent Application No. PCT/US2016/066248 filed Dec. 13, 2016, which claims benefit of U.S. Provisional Application No. 62/269,419, filed Dec. 18, 2015, the contents of which are hereby incorporated by reference in its entirety.

BACKGROUND OF THE INVENTION

Rotavirus infections are associated with diarrhea and vomiting in young children, which can lead to severe dehydration and electrolyte disturbance and, in some cases, shock and death. Rotaviruses are the most common etiologic agent of severe acute diarrheal disease in children<2 years of age. Older children, as well as adults, may also become infected with rotavirus and develop associated pathologies. The incidence of rotavirus-associated morbidity and death disproportionately impacts children in developing countries due to their poor healthcare systems. Approximately 90% of rotavirus-associated fatalities occur in lower income countries in Africa and Asia; World Health Organization-Rotavirus Vaccines WHO Position Paper, *WHO Weekly Epidemiological Record* 88:49-64 (2013)).

Two live attenuated oral rotavirus vaccines are commercially available in different countries throughout the world—RotaTeq® (Rotavirus Vaccine, Live, Oral, Pentavalent; Merck and Co., Inc., Whitehouse Station, N.J.) and Rotarix® (Rotavirus Vaccine, Live, Oral, GlaxoSmithKline Biologicals, Rixensart, Belgium). The introduction of these vaccines has led to a substantial reduction in disease burden in high and middle income countries (Patel et al., *PLoS Medicine,* 9(10): e1001330, p 1-10 (2012); Giaquinto et al., *Human Vaccines* 7:734-748 (2012)). For this reason, the WHO recommends vaccination against rotavirus and inclusion of a rotavirus vaccine in all national immunization programs. See *WHO Weekly Epidemiological Record*, supra at 62 (2013). However, despite the availability of vaccines that reduce the likelihood of rotavirus infection or disease associated therewith, rotavirus remains a cause of death for approximately 450,000 children per year under the age of 5, particularly in the developing world. Id. at 50.

For worldwide distribution of rotavirus vaccines, it is necessary to formulate vaccines such that they are stable under a variety of environmental conditions. Due to frequent cold-chain failures in the developing world, there exists a need for improved vaccines formulations that are thermally stable. In addition, in countries that do have a robust cold chain, the development of thermally stable vaccines would provide the ability to withstand inadvertent exposures to elevated temperatures.

SUMMARY OF THE INVENTION

The present invention is related to thermally stable liquid rotavirus vaccine formulations, suitable for oral administration, that are stable for 7 days at 37° C., for 45 days at 25° C. and for 2 years or more at 2-8° C. (i.e., meet VVM7 requirements, as discussed, infra). The formulations of the invention comprise a pharmaceutically effective amount of at least one rotavirus reassortant or attenuated rotavirus strain, a pharmaceutically acceptable salt of calcium, sucrose, adipic acid, and sodium phosphate, wherein the pH of the formulation is from about 6.2 to about 6.7. In preferred embodiments of the invention, the rotavirus vaccine formulation comprises from about 1.0 mM to about 3.5 mM of a pharmaceutically acceptable salt of calcium, from about 0.5 M to about 2.0 M sucrose, from about 260 mM to about 700 mM adipic acid, and from about 10 mM to about 100 mM sodium phosphate. In particular embodiments, the formulation further comprises a non-ionic surfactant, such as polysorbate 80. In additional embodiments, the formulation comprises tissue culture medium. The formulations of the invention preferably do not contain any zinc.

In particular embodiments of the invention, the formulations comprise one or more rotavirus reassortants selected from the group consisting of: G1, G2, G3, G4, and P1A. In further embodiments, the rotavirus vaccine formulation comprises G1, G2, G3, G4, and P1A rotavirus reassortants.

One preferred embodiment of the invention relates to a rotavirus vaccine formulation which comprises: a) one or more rotavirus reassortants selected from the group consisting of: G1, G2, G3, G4, and P1A; b) about 1.5 M sucrose; c) about 465 mM adipic acid; d) about 10 mM sodium phosphate; and e) about 3 mM of a pharmaceutically acceptable salt of calcium; wherein the pH of the formulation is about 6.4 at 25° C. In further embodiments, the formulation further comprises about 0.01% of polysorbate 80.

The invention also relates to a method of reducing the likelihood of rotavirus infection or for preventing or reducing the likelihood or severity of rotavirus gastroenteritis in a child, comprising administering a formulation of the invention to the child. In particular embodiments of this aspect of the invention, the formulation is administered orally to an infant between the ages of 6 and 12 weeks of age. In some embodiments of the invention, the method further comprises the steps of: (a) waiting for a predetermined amount of time to pass; (b) administering an additional dose of the formulation to the child, and (c) optionally repeating steps (a) and (b) one or more times. In one preferred embodiment, the method comprises administering the rotavirus vaccine formulation to the child in a 3-dose series, wherein the child is 32 weeks of age or younger at the completion of the series.

The invention also relates to the use of a rotavirus vaccine formulation of the invention for the treatment or prophylaxis of disease associated with rotavirus infection, such as for the prevention of rotavirus gastroenteritis.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

As used throughout the specification and appended claims, the following definitions and abbreviations apply:

The term "treatment" refers to both therapeutic treatment and prophylactic or preventative measures. Individuals or patients "in need of" treatment include those already with a rotavirus infection, whether or not manifesting any clinical symptoms, as well as those at risk of being infected with rotavirus. Treatment of a patient with the rotavirus vaccine formulations of the invention includes one or more of the following: inducing/increasing an immune response against rotavirus in the patient, inducing a virus neutralizing antibody response against one or more rotaviruses, preventing, ameliorating, abrogating, or reducing the likelihood of the clinical manifestations of rotavirus in patients who have been infected with rotavirus, preventing or reducing the likelihood of developing gastroenteritis or other disease or complication associated with rotavirus infection, reducing the severity or duration of the clinical symptoms of rotavirus infection such as diarrhea, vomiting, fever, and abdominal pain, and preventing or reducing the likelihood of rotavirus infection.

The term "pharmaceutically effective amount" or "effective amount" means an amount whereby sufficient vaccine composition is introduced to a patient to produce a desired effect, including, but not limited to: inducing/increasing an immune response against rotavirus in the patient, inducing/increasing a virus neutralizing antibody response against rotavirus in a patient, preventing or reducing the likelihood of rotavirus infection, preventing, ameliorating or abrogating the clinical manifestations of rotavirus infection in patients who have been infected with rotavirus, or reducing the severity or duration of disease associated with rotavirus. One skilled in the art recognizes that this level may vary for prophylaxis versus therapy and may vary according to the patient's characteristics such as age, weight, etc.

The term "immune response" refers to a cell-mediated (T-cell) immune response and/or an antibody (B-cell) response.

The term "patient" refers to a mammal capable of being infected with rotavirus, that is to receive the rotavirus vaccine formulations described herein, e.g. a human. In preferred embodiments, the patient is a pediatric patient. In one preferred embodiments, the patient is between 6 and 32 weeks of age. As defined herein, a "patient" includes those already infected with rotavirus and those that may subsequently be exposed, i.e., at risk of exposure. A patient can be treated prophylactically or therapeutically. Prophylactic treatment provides sufficient protective immunity to reduce the likelihood or severity of a rotavirus infection or the effects thereof, e.g., gastroenteritis. Therapeutic treatment can be performed to reduce the severity of a rotavirus infection or the clinical effects thereof.

The term "about", when modifying the quantity (e.g., mM, or M) of a substance or composition, the percentage (v/v or w/v) of a formulation component, the pH of a solution/formulation, or the value of a parameter characterizing a step in a method, or the like refers to variation in the numerical quantity that can occur, for example, through typical measuring, handling and sampling procedures involved in the preparation, characterization and/or use of the substance or composition; through inadvertent error in these procedures; through differences in the manufacture, source, or purity of the ingredients employed to make or use the compositions or carry out the procedures; and the like. In certain embodiments, "about" can mean a variation of ±0.1, 0.2, 0.3, 0.4, 0.5, 1.0, 2.0, 3.0, 4.0, or 5.0 of the appropriate unit. In certain embodiments, "about" can mean a variation of ±0.1%, 0.5%, 1%, 2%, 3%, 4%, 5%, or 10%.

"VVM7 formulation" alternatively, "VVM7RotaTeq™" refers to a rotavirus vaccine formulation of the invention, which is stable for at least 7 days at 37° C., for 45 days at 25° C. and for 2 years or more at 2-8° C. To be considered stable, a vaccine formulation of the invention must maintain potency above its clinically determined end of expiration potency for the lengths of time specified for each temperature, i.e. the minimum potency necessary for efficacy as defined in clinical trials. (See Table 1 below. See also, Table 7 from RotaTeq Package Insert, Initial U.S. Approval 2006, Revised June 2013, Merck & Co., Inc. Whitehouse Station, N.J., USA).

TABLE 1

Minimum Dose Levels of RotaTeq ™ Reassortants

| Name of Reassortant | Minimum Dose Levels ($10^6$ infectious units) |
| --- | --- |
| G1 | 2.2 |
| G2 | 2.8 |
| G3 | 2.2 |
| G4 | 2.0 |
| P1A | 2.3 |

"RotaTeq™ commercial formulation" refers to the vaccine RotaTeq™ (Rotavirus vaccine, live, oral, pentavalent), manufactured by Merck & Co., Inc. (Whitehouse Station, N.J.) and first approved in 2006 for the prevention of rotavirus gastroenteritis caused by the G1, G2, G3 and G4 rotavirus serotypes in infants 6 to 32 weeks of age.

The following abbreviations are used herein and have the following meanings: ANC=acid neutralizing capacity, CI=confidence interval, GMT=geometric mean titer, PS80=polysorbate 80, SNA=serum neutralizing antibody; v/v=volume per volume, VVM=vaccine vial monitor, VVMC=vaccine vial monitor compatible, VVM7=vaccine vial monitor category 7 (as described below), WFI=water for injection; w/v=weight per volume.

BRIEF DESCRIPTION OF THE DRAWINGS

FIG. 1 shows calcium precipitation at 37° C. Rotavirus formulations with varying levels of calcium were visually observed for signs of precipitation (PPT) after 3, 7, 10, 14, 18 and 39 days of incubation at 37° C. Results showed calcium precipitation issues in formulations containing 4 mM Ca at pH 6.2, 6.4, and 6.7 as well as in formulations containing 3.75 mM Ca at pH 6.7.

FIG. 2 shows a statistical analysis of noninferiority of GMT for the serum neutralizing antibody response to reassortants rotavirus serotypes G1, G2, G3, G4 and P1A (per-protocol population) for the study described in Example 8. The primary objective of the study was to determine whether the vaccine-induced antibody responses at 42 days post-dose 3 were similar (non-inferior) in subjects who received VVM7RotaTeq™ (RotaTeq™ New Formulation) versus subjects who received the commercial formulation of RotaTeq™ (RotaTeq™ Current Formulation). Results showed that the VVM7 RotaTeq™ formulation was non-inferior to the commercial formulation of RotaTeq™ with respect to immunogenicity for all 5 serotypes.

FIG. 3 provides an immunogenicity summary for serum anti-rotavirus IgA for the study described in Example 8.

DETAILED DESCRIPTION OF THE INVENTION

The present invention relates to thermally stable rotavirus vaccine formulations with increased thermal stability relative to prior rotavirus vaccine formulations. In particular, the invention relates to a rotavirus vaccine formulation comprising one or more rotavirus reassortant or attenuated rotavirus strains, wherein each of the one or more rotavirus reassortant or attenuated rotavirus strains is stable for 7 days at 37° C., for 45 days at 25° C. and for 2 years or more at 2-8° C.

Vaccine Vial Monitors (VVMs) allow healthcare workers in the field the ability to make an informed decision regarding whether or not to use a vial of vaccine (WHO, 2002, *Technical Review of Vaccine Vial Monitor Implementation* 27 Mar. 2002, 1-47). VVMs are labels affixed to each vaccine unit and contain a temperature sensitive material to monitor cumulative heat exposure with time. Such cumulative heat exposure causes the inner portion of the label to darken over time, providing a visual indication of thermal stress the vaccine experienced. The rate of color change increases with temperature. When the color of the inner portion of the label matches or is darker then the outer portion of the label the vaccine has exceeded its allowable cumulative heat exposure and should be discarded. The ability to easily identify that a vaccine should be discarded due to excessive heat exposure is particularly important in areas where cold chain failures may occur, as the VVM is the only temperature monitor present from distribution, to storage, to administration of the vaccine. As a result of the utility of VVMs, UNICEF and the WHO issued a policy statement in 1999 recommending that countries purchasing vaccines request manufacturers to include VVMs that meet the WHO's specifications. See *Quality of the cold chain: WHO/UNICEF policy statement on the use of vaccine vial monitors in immunization services* (WHO/V&B/99.18).

Currently there are four vaccine vial monitors categories specified by the WHO, which are classified based on the number of days at 37° C. it takes to reach the end point (Table 2). Due to the limited availability of commercial VVMs, a vaccine must be formulated to match the stability profile specified by the VVM. In order for a vaccine to meet the VVM stability criteria, it must maintain potency above its clinically determined end of expiration potency for the lengths of time specified for 2-8° C., 25° C. and 37° C. See Table 1, supra, for end of expiry potencies for RotaTeq™.

TABLE 2

Vaccine Vial Monitor Stability Requirements

| VVM | 37° C. | 2-8° C. | 25° C. |
|---|---|---|---|
| 2 | 2 days | 225 days | N/A |
| 7 | 7 days | >2 years | 45 days |
| 14 | 14 days | >3 years | 90 days |
| 30 | 30 days | >4 years | 193 days |

The present invention relates to a thermally stable oral rotavirus vaccine formulation with a stability profile that is compatible with the vaccine vial monitor category VVM7 (7 days at 37° C., 45 days at 25° C. and 2 years at 2-8° C.). Our strategy for developing a new rotavirus vaccine formulation that meets VVM7 stability requirements involved increasing free calcium concentration to increase thermal stability of the vaccine. We accomplished this by both selection of excipients with lower calcium binding constants than those in the current commercial RotaTeq™ formulation and the addition of calcium. The formulations of the invention comprise calcium and additional excipients, wherein the additional excipients are present in an amount that maximizes the calcium free in solution to stabilize the rotavirus particles. It is shown herein that the calcium binding affinity of the excipients used in the formulation has a direct impact on stability. The formulations of the invention provide a balance of calcium solubility and rotavirus stability. In preferred embodiments of the invention, the rotavirus formulations do not comprise zinc.

In particular embodiments of the invention, the oral rotavirus formulations comprise (in addition to rotavirus components) sodium adipate, sodium phosphate, calcium chloride and polysorbate 80. In a preferred embodiment of this aspect of the invention, the oral rotavirus vaccine formulation comprises 0.465M disodium adipate (generated in solution by neutralizing adipic acid with sodium hydroxide), 10 mM sodium phosphate, 3 mM calcium chloride and 0.01% (w/v) PS-80 at pH 6.4. An oral rotavirus vaccine formulation of the invention can be prepared using a cell-free preparation of live, rotavirus monovalent vaccine bulks, produced by the harvest and freeze-thaw lysis of rotavirus-infected Vero cell cultures, followed by filtration and concentration of the lysate. Individual rotavirus monovalent vaccine bulks for the desired active ingredients (i.e. rotavirus reassortant(s) and/or attenuated rotavirus strains) can be combined by mixing with a formulation buffer to manufacture a final drug product.

Various rotavirus vaccine formulations have been described. However, there exists a need for a rotavirus vaccine formulation that meets VVM7 requirements, consistent with the policy of the World Health Organization. Such a formulation would have a positive impact on world health by providing the ability to safely distribute rotavirus vaccines worldwide that are stable under a variety of environmental conditions and less susceptible to decreased potency and/or safety due to frequent cold-chain failures in the developing world.

We hypothesized that addition of calcium may have a beneficial impact on the thermal stability of a rotavirus vaccine formulation. However, prior disclosures have indicated that calcium may not have any impact on the stability of particular rotavirus formulations or may impact stability only under certain conditions. Burke et al. (U.S. Pat. Nos. 6,616,931 and 5,932,223) disclose that addition of 10 mM calcium improved the stability of rotavirus reassortants P1 and G1 when added to formulations that do not contain tissue culture media. The potency losses for both the G1 and P1 rotavirus reassortants were evaluated in the presence and absence of calcium chloride. When the rotavirus reassortants were dialyzed into 10 mM Tris with 100 mM sodium chloride, an improvement in stability at 37° C. was observed with addition of 10 mM calcium chloride. The potency log loss after three days at 37° C. was decreased more than four-fold (2.2 vs. 0.5) for P1 and more than twelve-fold (2.5 to 0.2) for G1. In contrast, when the G1 and P1 rotavirus reassortants were in a William's Medium E background, no improvement in stability was observed with addition of 10 mM calcium chloride. Additionally, WO2006/087205 discloses rotavirus vaccine formulations wherein calcium did not have a beneficial impact on stability.

In accordance with the invention, it is shown herein that specific amounts of calcium increase the stability of the rotavirus viral particles without inducing precipitation, thus allowing preparation of a thermally stable formulation that meets VVM7 requirements. In the formulations herein, calcium is present as a pharmaceutically acceptable salt of calcium. As used herein, the term "pharmaceutically acceptable" refers to a substance, as described throughout the specification, which is admixed with an active ingredient (e.g. a rotavirus reassortant) of the invention that is suitable for administration to humans. A pharmaceutically acceptable salt of calcium is safe and effective for the desired purpose (i.e. increasing stability). Examples of pharmaceutically acceptable calcium salts useful in the formulations of the invention include, but are not limited to: calcium chloride, calcium acetate, calcium carbonate, calcium citrate, calcium gluconate, calcium lactate and calcium sulfate. It is preferred that the calcium salt not be calcium phosphate in the formulations of the invention, due to its poor solubility, especially in the presence of sodium phosphate contained in this invention to increase acid neutralizing capacity. In preferred embodiments, the pharmaceutically acceptable calcium salt is in the form of calcium chloride.

WO 2013/02933 ("the '933 application") discloses that excess calcium ions in rotavirus vaccine formulations ensure vaccine viability at elevated temperatures. The '933 application states that the preferred amount of calcium in a rotavirus formulation to ensure viral stability is at least 4 mM. In accordance with the invention, it has been shown that an amount of less than 4 mM of calcium, i.e. from about 1.0 mM to about 3.8 mM calcium can stabilize a rotavirus vaccine without inducing precipitation. It is further shown herein that amounts of calcium of 4 mM or higher are not preferred as the calcium precipitates out of solution. See Examples 1 and 4.

To that end, the invention provides vaccine formulations, e.g. rotavirus vaccine formulations comprising one or more rotavirus reassortant or attenuated rotavirus strains, wherein the formulation components are as defined in any of the preceding embodiments and calcium is present in any of the following amounts: about 1.0 to about 3.8 mM, about 1.25 to about 3.8 mM, about 1.75 to about 3.8 mM, about 2.0 to about 3.8 mM, about 2.25 to about 3.8 mM, about 2.5 to about 3.8 mM, about 2.75 to about 3.8 mM, about 3.0 to about 3.8 mM, about 1 to about 3.5 mM, about 1.25 to about 3.5 mM, about 1.75 to about 3.5 mM, about 2.0 to about 3.5 mM, about 2.25 to about 3.5 mM, about 2.5 to about 3.5 mM, about 2.75 to about 3.5 mM, about 3.0 to about 3.5 mM, about 1 to about 3.0 mM, about 1.25 to about 3.0 mM, about 1.75 to about 3.0 mM, about 2.0 to about 3.0 mM, about 2.25 to about 3.0 mM, about 2.5 to about 3.0 mM, and from about 2.75 to about 3 mM. In alternative embodiments of the invention, the vaccine formulation components are as described in any preceding embodiment and the amount of calcium is about 1 mM, about 2 mM, about 2.5 mM, about 2.75 mM, about 3.0 mM, about 3.5 mM or about 3.75 mM. In preferred embodiments, the compositions comprise 3.0 mM calcium.

It is shown herein that the rotavirus vaccine formulations of the invention, which comprise a pharmaceutically acceptable salt of calcium in an amount specified above, (e.g. about 1.0 to about 3.8 mM) are stable even when the formulation comprises tissue culture media as diluent. Thus, the formulations of the present invention optionally comprise tissue culture media in an amount of from about 2 to about 30% v/v. Any tissue culture medium that is suitable for use in pharmaceutical formulations may be employed in the formulations of the invention, e.g. William's Medium E, Dulbecco's Modified Eagle's Medium, medium described in U.S. Pat. No. 6,656,719. Prior art disclosures (U.S. Pat. Nos. 6,616,931 and 5,932,223) have contrarily shown that calcium improved stability of specific rotavirus reassortants P1 and G1 when added to formulations that do not contain tissue culture media, but did not stabilize the G1 and P1 rotavirus reassortants when the formulation comprised William's Medium E.

The vaccine formulations of the invention comprise, as active ingredient(s), a pharmaceutically effective amount of at least one rotavirus reassortant or attenuated rotavirus strain (referred to herein as "rotavirus active ingredient(s)"). In embodiments of the invention, including any of the embodiments described above, the rotavirus vaccine formulation comprises one or more rotavirus reassortants. In alternative embodiments, the rotavirus formulation comprises at least one attenuated rotavirus strain.

The rotavirus parent strains of the reassortants can be isolated from appropriate human and bovine hosts. For example, the human rotavirus parent strain can be WI78, WI79, BrB, or SC2. The bovine rotavirus parent strain can be, for example, strain WC3. The rotavirus reassortant can be a reassortant rotavirus expressing an outer capsid protein from the human rotavirus parent strain and the attachment protein from the bovine rotavirus parent strain.

In one embodiment of the invention, the formulation comprises a reassortant rotavirus expressing the outer capsid proteins G1 from the human rotavirus parent strain and the attachment protein from the bovine rotavirus parent strain. In particular embodiments, the attachment protein from the bovine rotavirus parent strain is from serotype P7. As used herein, the term "G1" or "G1 reassortant" refers to a reassortant comprising G1 outer surface protein from a human rotavirus strain and an attachment protein from serotype P7 from a bovine parent strain.

In another embodiment of the invention, the formulation comprises a reassortant rotavirus expressing the outer capsid protein G2, from the human rotavirus parent strain and the attachment protein from the bovine rotavirus parent strain. In particular embodiments, the attachment protein from the bovine rotavirus parent strain is from serotype P7. As used herein, the term "G2 reassortant" refers to a reassortant comprising G2 outer surface protein from a human rotavirus strain and an attachment protein from serotype P7 from a bovine parent strain.

In a further embodiment, the formulation comprises a reassortant rotavirus expressing the outer capsid protein G3, from the human rotavirus parent strain and the attachment protein from the bovine rotavirus parent strain. In particular embodiments, the attachment protein from the bovine rotavirus parent strain is from serotype P7. As used herein, the term "G3 reassortant" refers to a reassortant comprising G3 outer surface protein from a human rotavirus strain and an attachment protein from serotype P7 from a bovine parent strain.

In yet another embodiment, the formulation comprises a reassortant rotavirus expressing the outer capsid protein G4, from the human rotavirus parent strain and the attachment protein from the bovine rotavirus parent strain. In particular embodiments, the attachment protein from the bovine rotavirus parent strain is from serotype P7. As used herein, the term "G4 reassortant" refers to a reassortant comprising G4 outer surface protein from a human rotavirus strain and an attachment protein from serotype P7 from a bovine parent strain.

In still a further embodiment, the formulation comprises a reassortant virus expressing the attachment protein, P1A (genotype P[8]), herein referred to as serotype P1A[8], from the human rotavirus parent strain and the outer capsid protein of serotype G6 from the bovine rotavirus parent strain. As used herein, the term "P1A[8] reassortant" refers to a reassortant comprising the outer surface protein from a bovine rotavirus strain and an attachment protein P1A (genotype P[8]), from a human parent strain.

In the formulations of the invention, each rotavirus active ingredient is individually present in a pharmaceutically effective amount. In preferred embodiments, the aggregate amount of all rotavirus active ingredients is from about $1 \times 10^6$ infectious units per mL to about $50 \times 10^6$ infectious units per mL. In preferred embodiments, the individual amount of each reassortant in the vaccine formulation is from about $2\times10^6$ to about $20\times10^6$ so that the amount per reassortant at the end of the expiry period is at least $2\times10^6$ infectious units per mL. In some embodiments, the formulation comprises a minimum of $2.0$-$2.8\times10^6$ infectious units per individual reassortant dose.

In selected embodiments, the formulation comprises at least one rotavirus reassortant selected from the group consisting of: G1, G2, G3, G4, and P1A. In some embodiments, the formulation comprises two or more rotavirus reassortants selected from the group consisting of: G1, G2, G3, G4, and P1A. In other embodiments, the formulation comprises three or more rotavirus reassortants selected from the group consisting of: G1, G2, G3, G4, and P1A. In further embodiments, the formulation comprises four or more rotavirus reassortants selected from the group consisting of: G1, G2, G3, G4, and P1A. In still further embodiments, the formulation comprises G1, G2, G3, G4, and P1A rotavirus reassortants.

The rotavirus reassortants can be propagated using standard cell culture techniques in the absence of antifungal agents, for example, propagation in Vero cells.

As stated supra, one goal in developing a rotavirus vaccine formulation that meets VVM7 stability requirements was to increase free calcium concentration to increase thermal stability of the vaccine. A second goal was to develop a formulation with sufficient acid neutralizing capacity (ANC) to ensure the active pharmaceutical ingredients (i.e. viral reassortants) reach the small intestine intact. Since the intended rotavirus vaccine formulations are for oral administration, each of the active reassortants must survive the harsh environment of the stomach to enter the small intestine. Previous studies indicated that several bovine rotavirus strains, including WC3, the backbone of the human-bovine reassortants in the current RotaTeq™ formulation, are rapidly inactivated in acidic conditions (below pH 4.0). Weiss, S., Clark, H. F. "Rapid Inactivation of Rotaviruses by Exposure to Acid Buffer or Acidic Gastric Juice" *Journal of General Virology* 66: 2725-2730 (1985).

Due to the requirement for sufficient ANC as described above, the commercial formulation of RotaTeq™ includes both sodium citrate and sodium phosphate to neutralize infant stomach acid so that the virus does not degrade prior to arriving in the small intestine; thus allowing the generation of a protective immune response. In the development of the VVM7 formulation herein, we decided that inclusion of sodium citrate would not be optimal because it has a relatively high calcium binding constant compared to other carboxylic acids. We decided to substitute citrate with a lower calcium affinity carboxylic acid to provide the required acid neutralization, but improve virus stability by leaving more calcium in solution.

To that end, in embodiments of the invention, the rotavirus vaccine formulation comprises the dicarboxylate adipic acid instead of the tricarboxylate sodium citrate in the RotaTeq™ formulation because adipic acid has a lower calcium binding constant compared to sodium citrate and has an acceptable safety profile. In specific embodiments of the invention, the rotavirus vaccine formulations comprise components as defined in any preceding embodiment or any embodiment described below (and combinations thereof), and further comprise about 260 mM to about 700 mM adipic acid.

In some embodiments, the formulation comprises adipic acid in an amount from about 275 mM to about 700 mM, from about 300 mM to about 700 mM, from about 325 mM to about 700 mM, from about 350 mM to about 700 mM, from about 400 mM to about 700 mM, from about 425 mM to about 700 mM, from about 450 mM to about 700 mM, from about 275 mM to about 650 mM, from about 300 mM to about 650 mM, from about 325 mM to about 650 mM, from about 350 mM to about 650 mM, from about 400 mM to about 650 mM, from about 425 mM to about 650 mM, from about 275 mM to about 600 mM, from about 300 mM to about 600 mM, from about 325 mM to about 600 mM, from about 350 mM to about 600 mM, from about 400 mM to about 600 mM, from about 425 mM to about 600 mM, from about 450 mM to about 600 mM, from about 275 mM to about 550 mM, from about 300 mM to about 550 mM, from about 325 mM to about 550 mM, from about 350 mM to about 550 mM, from about 400 mM to about 550 mM, from about 425 mM to about 550 mM, from about 450 mM to about 550 mM, from about 275 mM to about 500 mM, from about 300 mM to about 500 mM, from about 325 mM to about 500 mM, from about 350 mM to about 500 mM, from about 400 mM to about 500 mM, from about 425 mM to about 500 mM, or from about 450 mM to about 500 mM. In one particular preferred embodiment, the rotavirus vaccine formulation comprises about 465 mM adipic acid.

In specific embodiments of the invention, the rotavirus vaccine formulations comprise components as defined in any preceding embodiment or any embodiment described below (and combinations thereof), and further comprise about 0.5 M to about 2.0 M sucrose. Sucrose is added to the formulation to increase overall viral stability. In additional embodiments, the concentration of sucrose in the composition is about 0.5 M to about 1.9 M, about 0.5 mM to about 1.8M, about 0.5 mM to about 1.75M, about 0.5 M to about 1.6M, about 0.5 M to about 1.5M; 0.75 M to about 1.9 M, about 0.75 mM to about 1.8M, about 0.75 mM to about 1.75M, about 0.75 M to about 0.75, about 0.75 to about 1.5M, 1.0 M to about 1.9 M, about 1.0 mM to about 1.8M, about 1.0 mM to about 1.75M, about 1.0 M to about 1.6M, about 1.0 mM to about 1.5M; 1.25 mM to about 1.75M, about 1.25 M to about 1.6M, or about 1.25 M to about 1.5M.

In alternative embodiments, the vaccine composition comprises about 0.5M, about 1.0M, about 1.25M, about 1.5M about 1.75M, or about 2M sucrose. In one preferred embodiment, the vaccine formulation comprises about 1.5M sucrose.

The formulations of the invention may also comprise sodium phosphate, which contributes to the ANC of the solution. Sodium phosphate may be in the form of sodium phosphate monobasic monohydrate. Thus, in further embodiments of the invention, the rotavirus vaccine formulations comprise excipients as defined in any preceding embodiment or any embodiment described below (and combinations thereof), and further comprise from about 10 mM to about 100 mM sodium phosphate. The use of about 10 mM to about 100 mM sodium phosphate, in combination with about 1.0 to about 3.8 mM calcium salt, and about 275 mM to about 700 mM adipic acid maximizes soluble calcium concentration without inducing precipitation, allowing the formulation to meet VVM7 requirements. In preferred embodiments of the invention, the formulation comprises about 10 mM sodium phosphate. In further embodiments, the formulation comprises about 5 mM sodium phosphate, about 15 mM sodium phosphate, about 20 mM sodium phosphate, about 25 mM sodium phosphate, about 50 mM sodium phosphate, about 75 mM sodium phosphate, or about 100 mM sodium phosphate.

Any of the vaccine formulations described herein may optionally comprise a surfactant. Surfactants may be added to vaccine formulations to provide stability, reduce and/or prevent aggregation or to prevent and/or inhibit protein damage during processing conditions such as purification, filtration, freeze-drying, transportation, storage, and delivery. In the present invention, a surfactant may be useful for providing additional stability to the rotavirus active ingredient(s).

Surfactants that may be useful in the formulations of the invention include, but are not limited to: nonionic surfactants such as polyoxyethylene sorbitan fatty acid esters (Polysorbates, sold under the trade name Tween® (Uniquema Americas LLC, Wilmington, Del.)) including Polysorbate-20 (polyoxyethylene sorbitan monolaurate), Polysorbate-40 (polyoxyethylene sorbitan monopalmitate), Polysorbate-60 (polyoxyethylene sorbitan monostearate), and Polysorbate-80 (polyoxyethylene sorbitan monooleate); polyoxyethylene alkyl ethers such as Brij® 58 (Uniquema Americas LLC, Wilmington, Del.) and Brij® 35; poloxamers (e.g., poloxamer 188); Triton® X-100 (Union Carbide Corp., Houston, Tex.) and Triton® X-114; NP40; Span 20, Span 40, Span 60, Span 65, Span 80 and Span 85; copolymers of ethylene and propylene glycol (e.g., the Pluronic® series of nonionic surfactants such as Pluronic® F68, Pluronic® 10R5, Pluronic® F108, Pluronic® F127, Pluronic® F38, Pluronic® L44, Pluronic® L62 (BASF Corp., Ludwigshafen, Germany); and sodium dodecyl sulfate (SDS).

The amount of surfactant to be included in the formulations of the invention is an amount sufficient to perform the desired function, i.e. a minimal amount necessary to stabilize the rotavirus reassortant(s) or attenuated rotavirus strain in the formulation. Typically, the surfactant is present in a concentration of from about 0.008% to 0.04% w/v (wt/vol). In some embodiments of this aspect of the invention, the surfactant is present in the formulation in an amount from about 0.01% to about 0.04%; from about 0.01% to about 0.03%, or from about 0.01% to about 0.02%. In specific embodiments, the surfactant is present in an amount of about 0.01%. In alternative embodiments, the surfactant is present in an amount of 0.015%, 0.02%, 0.025%, 0.03%, 0.035%, or 0.04%.

In exemplary embodiments of the invention, the surfactant is a nonionic surfactant selected from the group consisting of: Polysorbate 20, Polysorbate 80, Brij®35, Pluronic® F-68 and Triton®. In some embodiments, the surfactant is Polysorbate 20 or Polysorbate 80. In specific embodiments, the rotavirus vaccine formulation comprises about 0.01% PS80.

The pH of the vaccine compositions of the invention at 25° C., as described in any preceding embodiment or any embodiment described below, is preferably in the range of about 6.2 to about 6.7. Stability studies described herein (see example 2) demonstrate that greater potency loss rates were observed for particular rotavirus reassortants at pH's as low as 6.0 or as high as 7.0. Specifically, the G1, G4 and P1 reassortants showed greater losses at pH 6.0 and pH 7.0. Thus, the formulations of the invention are kept at a pH higher than 6.0 and lower than 7.0 in order to provide lower potency loss rates for all rotavirus active ingredients. In specific embodiments of the invention, the pH of the composition is about 6.2 to about 6.6, about 6.2 to about 6.5, about 6.2 to about 6.4, about 6.2 to about 6.3, about 6.3 to about 6.7 about 6.3 to about 6.6 or about 6.3 to about 6.5. In additional embodiments, the pH is about 6.2, about 6.3, about 6.4, about 6.5, about 6.6 or about 6.7. In particular embodiments, the pH of the formulation at 25° C. is about 6.4.

The pH of the formulations of the invention may be adjusted to optimal levels through the addition of various pharmaceutically acceptable excipients that are useful as acidifying and alkalizing agents, which lower or increase the pH of the formulation, respectively. Alkalizing agents useful for increasing the pH of the formulation include: ammonia solution, ammonium carbonate, diethanolamine, monoethanolamine, potassium hydroxide, sodium bicarbonate, sodium borate, sodium carbonate, sodium hydroxide, sodium phosphate dibasic and trolamine. In embodiments of the invention, the pH is adjusted through the addition of sodium hydroxide. In embodiments of the invention, the amount of sodium hydroxide is from about 750 mM to about 1.25 M. In particular embodiments, the amount of sodium hydroxide is from about 900 mM to about 950 mM. In additional embodiments the amount of sodium hydroxide is about 924 mM.

WO2006/042202 reports that zinc was a key excipient to impart stability on the rotavirus vaccine formulations described therein. Similarly, WO2013/029033 states that it is preferred to have zinc in a rotavirus vaccine formulation. We discovered, surprisingly, that zinc was actually detrimental to the stability of the rotavirus formulations herein (see Example 5). The stability of an exemplary pentavalent rotavirus vaccine formulation containing 465 mM adipic acid, 100 mM sodium phosphate, 1.5 M sucrose, 0.01% PS80 and 2 mM calcium chloride at pH 6.7 was evaluated in the presence and absence of 1 mM zinc chloride. Rotavirus potency data was used to calculate potency loss rates of each reassortant in the test formulations. The data showed that all 5 reassortants had greater potency losses after 7 days at 37° C. when 1 mM zinc was included in the formulation. Accordingly, it is preferred that the formulations of the invention do not include zinc.

Methods of Use

The present invention also provides a method of preventing or reducing the likelihood of infection of a human patient by a rotavirus comprising administration of a vaccine formulation as disclosed herein. The invention also provides a method of preventing or reducing the likelihood of rotavirus gastroenteritis, or reduction of the duration or severity thereof comprising administration of a vaccine formulation as disclosed herein. In specific embodiments of the methods provided herein, the pharmaceutical composition that is administered to the patient comprises one or more rotavirus reassortant or attenuated rotavirus strains. In one embodiment, the vaccine formulation comprises at least one rotavirus reassortant. In another embodiment, the vaccine formulation comprises G1, G2, G3, G4, and P1A rotavirus reassortants.

In some embodiments of this invention, the rotavirus pharmaceutical formulations disclosed herein are administered orally to a patient in various prime/boost combinations in order to induce an enhanced, durable, immune response. In this case, two or more pharmaceutical compositions or formulations are administered in a "prime and boost" regimen. For example the first composition is administered one or more times, then after a predetermined amount of time, for example, 2 weeks, 1 month, 2 months, six months, or other appropriate interval, a second composition is administered one or more times. Preferably, the two or more rotavirus pharmaceutical compositions used in a clinical regimen are administered at 4 to 10 week intervals, with the first dose being administered at 6 to 12 weeks of age. In specific embodiments of the invention, the vaccine composition is administered three times with the third dose being administered at age 32 weeks of age or less.

Thus, the invention relates to a method of reducing the likelihood of rotavirus infection or for preventing or reducing the likelihood of rotavirus gastroenteritis in a child, or the severity or duration thereof, comprising administering any rotavirus vaccine formulation of the invention to the child orally. In specific embodiments of this aspect of the invention, the child is an infant between the ages of 6 and 32 weeks of age. In other embodiments, the child is an infant between the ages of 6 and 12 weeks of age.

In another embodiment of the invention, the method above further comprises the steps of: (a) waiting for a predetermined amount of time to pass; (b) administering an additional dose of the formulation to the child, and (c) optionally repeating steps (a) and (b). The amount of time between the first dose of a rotavirus vaccine composition of the invention and the second dose of a rotavirus vaccine composition of the invention, or any dose thereafter, can vary. In particular embodiments, the first administration is given to a child that is about 6 to about 12 weeks of age. In further embodiments, the method comprises administering the rotavirus vaccine formulation to the child in a 3-dose series, wherein the child is 32 weeks of age or younger at the completion of the series.

In any embodiment of the methods of the invention, the rotavirus vaccine formulation is optionally concomitantly administered to the child with a one or more additional vaccines comprising one or more of the following: diphtheria and tetanus toxoids and acellular pertussis (DTaP), inactivated poliovirus vaccine (IPV), *Haemophilus* influenza type b conjugate (Hib), hepatitis B vaccine, pneumococcal conjugate vaccine.

The invention also relates to the use of the rotavirus vaccine formulation of any embodiment described in the specification for the treatment or prophylaxis of disease associated with rotavirus infection. The invention also relates to the use of the rotavirus vaccine formulations of the invention for the prevention of rotavirus gastroenteritis.

Embodiments of the invention also include one or more of the rotavirus vaccine formulations described herein (i) for use in, (ii) for use as a medicament or composition for, or (iii) for use in the preparation of a medicament for: (a) therapy (e.g., of the human body); (b) medicine; (c) inhibition of rotavirus replication, (d) induction of an immune response or a protective immune response against rotavirus; (e) induction of a virus neutralizing antibody response against rotavirus; (f) treatment or prophylaxis of infection by rotavirus; (g) reduction of the progression, onset or severity of pathological symptoms associated with rotavirus infection and/or reduction of the likelihood of a rotavirus infection or, h) treatment, prophylaxis of, or delay in the onset, severity, or progression of rotavirus-associated disease(s), including, but not limited to: gastroenteritis.

Accordingly, the invention provides methods for the prophylactic and/or therapeutic treatment of rotavirus infection or rotavirus-associated disease comprising administering one or more of the formulations of the invention to a patient in need of treatment.

Prophylactic treatment can be performed using a rotavirus vaccine formulation of the invention, as described herein. The formulation of the invention can be administered to the general population or to those persons at an increased risk of rotavirus infection.

Accordingly, the invention provides a method for inducing a protective immune response in a patient against a rotavirus infection comprising the step of administering to the patient a pharmaceutically effective amount of any of the rotavirus vaccine formulations described herein.

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

Example 1

VVMC Rotavirus Formulation Excipient Selection

We evaluated the amount of time for the commercial vaccine formulation (Rotateq™) to reach expiry potency starting from the minimum release potency. It was determined that although each reassortant in the vaccine was stable for the requisite period of time to meet VVM7 when stored at 5° C., all five reassortants failed to meet the minimum VVM7 requirements at 25° C. and 37° C. Thus, studies were undertaken to reformulate the commercial rotavirus vaccine to increase the thermal stability profile of the product to match VVM7 requirements, which necessitates that vaccine potency stay above end of expiry for all five reassortants after storage for 7 days at 37° C., 45 days at 25° C. or 2 years at 2-8° C.

Since RotaTeq™ is administered orally, each of the active reassortants must survive the harsh environment of the stomach to enter the small intestine. It was previously demonstrated that several bovine rotavirus strains, including WC3, the backbone of the human-bovine reassortants used in RotaTeq™, are rapidly inactivated in acidic conditions (below pH 4.0). Weiss, S., Clark, H. F. "Rapid Inactivation of Rotaviruses by Exposure to Acid Buffer or Acidic Gastric Juice" *Journal of General Virology* 66: 2725-2730 (1985). As a result, the commercial formulation of RotaTeq™ includes both sodium citrate and sodium phosphate to neutralize infant stomach acid so that the virus does not degrade prior to arriving in the small intestine; thus allowing the generation of a protective immune response. One goal in developing the VVM7 formulation was to meet or exceed the acid neutralizing capacity (ANC) of the commercial RotaTeq™ formulation, which is 0.86 mEQ/dose, to ensure the active pharmaceutical ingredients (i.e. viral reassortants) reach the small intestine intact.

Our strategy for developing a new RotaTeq™ formulation that meets VVM7 stability requirements involved increasing free calcium concentration to increase thermal stability of the vaccine. We accomplished this by both selection of excipients with lower calcium binding constants then those in the commercial RotaTeq™ formulation and the addition of calcium chloride. Sodium citrate, which is used in the commercial RotaTeq™ formulation for acid neutralization, has a relatively high calcium binding constant compared to other carboxylic acids. We decided to substitute sodium citrate with a lower calcium affinity carboxylic acid to provide the required acid neutralization, but improve virus stability by leaving more calcium in solution. The dicarboxylate adipic acid was selected to replace the tricarboxylate citrate in the RotaTeq™ formulation because of its lower calcium binding constant and its safety profile. The calcium binding constant of adipic acid (log(K) is 2.19 and K is ~155) is roughly 20-fold lower than that of citric acid (log(K) is 3.5 and K is 3162).

The second approach utilized to maximize the free calcium in the formulation available to stabilize the infectious rotavirus particles was to add calcium chloride to the formulation. However, because increasing the concentration of calcium in a formulation that also contains phosphate can result in calcium phosphate precipitation, we initiated a series of precipitation screening studies to determine what combination of calcium, phosphate, and adipic acid concentrations would maximize soluble calcium without the risk of precipitation.

Two concentrations of adipic acid were initially tested during formulation development: 465 mM and 250 mM. The use of 465 mM adipic acid resulted in a formulation with significantly higher ANC relative to the commercial formulation. A concentration of 250 mM of adipic acid, which would decrease the ANC of the formulation to a level similar to that of the commercial RotaTeq™ formulation, was also tested. A significant decrease in calcium solubility (from 3.0 mM to 1.5 mM) was observed with the test formulation comprising 250 mM adipic acid; thus, 465 mM adipic acid was selected as the target concentration.

The first studies to maximize soluble calcium concentration in a phosphate containing formulation were carried out using sodium phosphate to match the concentration in the commercial RotaTeq™ formulation. These studies used a base formulation of 465 mM adipic acid, 100 mM sodium phosphate, 1.5 M sucrose and 0.01% (w/v) polysorbate 80. Test formulations were prepared in which the pH varied from 6.0 to 6.7 and the calcium concentration was either 1.0, 2.0, or 3.0 mM. Formulations were observed for the formation of precipitate upon incubation at 25 and 37° C. Formulations containing 2 and 3 mM calcium at pH 6.5 and 6.7 routinely showed precipitation at both incubation temperatures. These observations indicated that 1 mM calcium is the maximum concentration of calcium that can be added to a formulation containing 100 mM phosphate. Precipitation was observed first in samples at pH 6.7 that had been incubated at 37° C. Thus, subsequent screens were focused on evaluating precipitate formation at pH 6.7 with incubation at 37° C.

In a second set of experiments the concentration of phosphate in the formulation was varied along with calcium concentration with the goal of identifying the combination that maximized soluble calcium. The base formulations used in these studies contained 465 mM adipic acid, 1.5M sucrose and 0.01% (w/v) polysorbate 80 at pH values of 6.5 and 6.7. The sodium phosphate concentrations examined included 100 mM, 50 mM and 10 mM. The concentrations of calcium tested in this screen varied from 1 mM up to 4 mM. Once again, precipitation was observed in the 100 mM phosphate concentration formulations when the calcium concentration exceeded 1 mM. When the phosphate concentration was decreased to 50 mM, no significant improvement in calcium solubility was achieved as precipitation was observed in formulations containing more than 1 mM calcium. In contrast, a significant improvement in calcium solubility was observed in formulations containing only 10 mM phosphate where precipitation was not observed until 4.0 mM calcium was added. These studies indicate that significantly higher soluble calcium concentrations can be achieved when phosphate concentration is reduced to 10 mM.

Example 2

Impact of pH on Stability.

A stability study was conducted to generate stability data across the pH range (6.0 to 7.0) for the 465 mM adipic acid, 100 mM phosphate, 1.5 M sucrose, 0.01% PS-80 and 1 mM calcium formulation. Briefly, pentavalent rotavirus formulations were prepared at pH 6.0, 6.2, 6.5, 6.7 and 7.0 and filled into the oral dosing tubes. Stability of all 5 reassortants was evaluated after incubation at 37° C. for 0, 1, 2, 3, 6, 7, 8, and 10 days. Rotavirus potency data was used to calculate potency loss rates of each reassortant at the five pH values tested by performing a linear regression on the natural logarithmic transformed potencies by time (days). The natural log value of the average potency loss after 7 days of storage at 37° C. are reported below (Table 3). The G1, G4 and P1 reassortants showed greater losses at both ends of the pH range tested.

TABLE 3

Impact of pH on Stability
Average Potency Loss after 7 days at 37° C. (ln potency loss)

| Reassortant | pH 6.0 | pH 6.2 | pH 6.5 | pH 6.7 | pH 7.0 |
| --- | --- | --- | --- | --- | --- |
| G1 | 0.78 | 0.40 | 0.60 | 0.50 | 1.17 |
| G2 | 0.70 | 0.57 | 0.41 | 0.32 | 0.53 |
| G3 | 0.39 | 0.45 | 0.21 | 0.31 | 0.53 |
| G4 | 0.64 | 0.41 | 0.33 | 0.60 | 0.77 |
| P1 | 0.62 | 0.30 | 0.31 | 0.22 | 0.62 |

Example 3

Adipic Acid Concentration

The impact of adipic acid concentration on the stability of rotavirus reassortants was evaluated at 250 mM, 350 mM, 465 mM, and 700 mM adipic acid in the presence of 10 mM phosphate, 1.5 M sucrose, 0.01% PS80 and 3 mM calcium at pH 6.4. Briefly, pentavalent rotavirus formulations were prepared and filled into the oral dosing tubes. Stability of all 5 reassortants was evaluated after incubation at 37° C. for 0, 3, 7, and 10 days. Rotavirus potency data was used to calculate potency loss rates of each reassortant at the four adipic acid concentrations tested by performing a linear regression on the natural logarithmic transformed potencies by time (days). The natural log values of the average potency loss after 7 days of storage at 37° C. are reported below for each reassortant (Table 4). The potency loss after 7 days at 37° C. were consistent across the range of adipic acid concentrations tested for the G1, G2 and G3 reassortants. This observation was unexpected since higher concentration of adipic acid would chelate higher amounts of calcium and could result in decreased stability. While not wishing to be bound by theory, one interpretation of this result is even at 700 mM adipic acid enough calcium remains in solution or associated with the virus particles so that there is no impact on stability. For the G4 reassortant the potency losses were slightly higher at higher concentrations of adipic acid.

TABLE 4

Impact of Adipic Acid Concentration on Stability
Average Potency Loss after 7 Days at 37° C. (ln potency loss)

| Reassortant | 250 mM Adipic Acid | 350 mM Adipic Acid | 465 mM Adipic Acid | 700 mM Adipic Acid |
| --- | --- | --- | --- | --- |
| G1 | 0.43 | 0.48 | 0.47 | 0.43 |
| G2 | 0.44 | 0.44 | 0.43 | 0.48 |
| G3 | 0.30 | 0.25 | 0.30 | 0.37 |
| G4 | 0.35 | 0.34 | 0.51 | 0.51 |
| P1 | ND | ND | ND | ND |

Example 4

Refinement of Calcium Phosphate Precipitation

We conducted another set of experiments with the primary objective to determine at what concentration (between 3 and 4 mM) calcium precipitation is first observed. In this set of experiments, a base formulation of 465 mM adipic acid, 10 mM sodium phosphate, 1.5 M sucrose and 0.01% (w/v) polysorbate 80 was used. Rotavirus formulations with varying levels of calcium were visually observed for signs of precipitation (PPT) after 3, 7, 10, 14, 18 and 39 days of incubation at 37° C. The calcium chloride concentrations tested in these studies ranged from 1 to 4 mM with particular focus on concentrations between 3 and 4 mM. For completeness, the pH of the formulation was varied from 6.2 to 6.7 and the occurrence of precipitation was monitored with incubation at 37° C. Results indicated that when samples contained 3.5 mM calcium or less, no precipitation was observed at any of the pH values tested, even after 39 days of incubation (see FIG. 1). We observed precipitation issues in formulations containing 4 mM Ca at either pH 6.2 or 6.4, as shown in the table below. At pH 6.7 we observed precipitation in formulations containing 3.75 and 4 mM. Therefore, the optimum calcium concentration for stability based on risk of precipitation and stability was selected to be 3 mM.

Example 5

Impact of Zinc on Stability

A stability study was conducted to assess if there was a benefit to including zinc in the rotavirus vaccine formulation. The stability of pentavalent rotavirus vaccine formulations containing 465 mM adipic acid, 100 mM phosphate, 1.5 M sucrose, 0.01% PS80 and 2 mM calcium chloride at pH 6.7 was evaluated in the presence and absence of or 1 mM zinc chloride. Stability of all 5 reassortants was evaluated after incubation at 37° C. for 0, 3, 7, and 8 days. Rotavirus potency data was used to calculate potency loss rates each reassortant in the 2 formulations tested by performing a linear regression on the natural logarithmic transformed potencies by time (days). Natural log of the average potency loss after 7 days of storage at 37° C. are reported in the below (Table 5). All 5 reassortants had greater potency losses after 7 days at 37° C. when 1 mM zinc was included in the formulation.

TABLE 5

Impact of Zinc on Stability
Average Potency Loss after 7 days at 37° C. (ln potency loss)

| Reassortant | 2 mM Ca | 2 mM Ca + Zn |
|---|---|---|
| G1 | 0.70 | 0.97 |
| G2 | 0.22 | 0.44 |
| G3 | 0.23 | 0.52 |
| G4 | 0.33 | 0.55 |
| P1 | 0.18 | 0.57 |

Example 6

Determination of Compatibility of Formulation with VVM7 Requirements

A formal stability study to evaluate potency loss rates at the requisite VVM temperatures (37° C., 25° C. and 2 to 8° C.) was conducted. For each temperature being evaluated, samples were incubated for varying amounts of time and the remaining potency was measured. Loss rates with 95% CI were determined using the measured potency values. The data presented in Table 6 and Table 7 summarizes the potency loss rates for the commercial RotaTeq™ formulation (which has high calcium binding affinity) and the VVMC formulation (low calcium binding affinity) at 37° C. and 25° C., respectively. Large improvements in stability were observed at 37° C. with the greatest improvement seen in the G3 reassortant (362-fold enhancement). More modest stability enhancements were observed at 25° C., where all reassortants showed loss rate improvements ranging from 1.7- to 51.1-fold. In summary, by maximizing the free calcium in solution available to stabilize the virus particles, the stability of all five rotavirus reassortants present in RotaTeq™ was improved at elevated temperatures, and resulted in a VVM7 compatible formulation.

TABLE 6

Infectivity Loss per

TABLE 8-continued

PS80 Concentration in Formulation Buffer and Final Containers

| Formulation | Theoretical Formulation Buffer Concentration | Final Container Concentration (experimentally determined; Lot1, Lot 2, Lot 3) |
|---|---|---|
| 3 | 0.010% (w/v) | 0.0136, 0.0139, 0.0142% (w/v) |
| 4 | 0.040% (w/v) | 0.0451, 0.0426, 0.0437% (w/v) |

Each of the 12 final container lots were placed on stability for 0 or 9 days at 37° C., after which potency of all five reassortants was determined. The PS80 concentration and potency results were analyzed to determine if stability was impacted by PS80 concentration in the range studied. Briefly, the potency data was fitted to a mixed effects regression model to test for statistical significance of the interaction term time formulation. Significance of this term indicates a potential difference in the loss rates across formulations. Results indicated that reassortants G1, G2, G3 and G4 had interaction term p-values greater than 0.05, indicating that significance was not found. Reassortant P1 had an interaction term p-value of 0.049, indicating borderline significance; thus, individual slope values were calculated for each lot and formulation. This further analysis showed that formulation #4 had consistently larger slope values across the three lots. With a borderline significant difference attributed to an improvement in stability at the high PS80 concentration, it was concluded that all reassortants were stable across the PS80 concentrations tested.

Example 8

Double-Blind, Randomized, Controlled, Study to Evaluate the Safety, Tolerability, and Immunogenicity of VVM7-RotaTeq™

The primary purpose of this study was to demonstrate the noninferiority of VVM7RotaTeq™ when compared with the commercial formulation of RotaTeq™ on the basis of immunogenicity. The primary objective of the study was to determine whether the vaccine-induced antibody responses at 42 days postdose 3 are similar (noninferior) in subjects who received VVM7RotaTeq™ versus subjects who received the commercial formulation of RotaTeq™.

Eligible subjects between 6 to 12 weeks of age were randomly assigned in a 1:1 ratio to 2 vaccination groups: Group 1 received 3 oral doses of the VVM7 RotaTeq™ and Group 2 received 3 oral doses of the commercial formulation of RotaTeq™. Sera was collected at 2 time intervals (prior to dose 1 and 42 days postdose 3) and tested by serum neutralizing antibody (SNA) to human rotavirus serotypes G1, G2, G3, G4, and P1A[8], as well as serum anti-rotavirus IgA. Safety and tolerability of the new formulation was also evaluated. Stool samples were collected and tested for rotavirus for subjects who experienced moderate to severe diarrhea and/or vomiting within 14 days of vaccination.

A total of 1020 subjects were randomized, and 1014 subjects were vaccinated. Among them, 510 received the new formulation and 504 received the current formulation of RotaTeq™. The two groups had generally comparable baseline characteristics.

The primary immunogenicity hypothesis was to demonstrate non-inferiority between groups with respect to the GMTs of vaccine-induced SNA responses to human rotavirus serotype G1, G2, G3, G4, and P1A[8] in subjects who received 3 doses of study vaccine. Success criteria required that the lower bound of the 95% CI of the GMT ratio be >0.67 (corresponding to a no more than 1.5-fold decrease in the GMT of the new formulation compared with the current formulation). The VVM7 RotaTeq™ formulation was non-inferior to the commercial formulation of RotaTeq™ with respect to immunogenicity for all 5 serotypes (see FIG. 2). The GMT for G3 was higher in the new formulation group compared to the current formulation group. In addition, the immunogenicity for serum anti-rotavirus IgA were similar in the new formulation group and the current formulation group (see FIG. 3).

Data was collected with regard to safety for subjects in both groups. Intussusception, diarrhea, vomiting, elevated temperature (rectal temperature 38.1° C. [100.5° F.] or equivalent), and irritability following any dose were pre-specified as events of interest. Results indicated that the VVM7 formulation was well-tolerated and had a comparable safety profile to the commercial RotaTeq™ formulation regarding these events. There were no vaccine-related serious adverse events and no deaths in the study. Only 2 subjects discontinued from the study due to an adverse event.

What is claimed is:

1. A liquid rotavirus vaccine formulation comprising a pharmaceutically effective amount of one or more rotavirus reassortants selected from the group consisting of: G1, G2, G3, G4, and P1A; about 3 mM of a pharmaceutically acceptable salt of calcium; about 1.5 M sucrose; about 465 mM adipic acid; and about 10 mM sodium phosphate; wherein the pH of the formulation is about 6.4 at 25° C.

2. The rotavirus vaccine formulation of claim 1, wherein the calcium is from calcium chloride.

3. The rotavirus vaccine formulation of claim 1, further comprising a non-ionic surfactant.

4. The rotavirus vaccine formulation of claim 3, wherein the non-ionic surfactant is polysorbate 80, which is present in a concentration of 0.008% to 0.04% w/v.

5. The rotavirus vaccine formulation of claim 3, wherein the non-ionic surfactant is polysorbate 80, which is present in a concentration of about 0.01% w/v.

6. The rotavirus vaccine formulation of claim 5, wherein the formulation comprises G1, G2, G3, G4, and P1A rotavirus reassortants.

7. The rotavirus vaccine formulation of claim 5, wherein the aggregate amount of rotavirus reassortants is from about $1.0 \times 10^6$ to about $50 \times 10^6$ infectious units per mL.

8. The rotavirus vaccine formulation according to claim 1, further comprising tissue culture media.

9. The rotavirus vaccine formulation according to claim 8, wherein the tissue culture media is present in an amount from about 2 to about 30% v/v.

10. The rotavirus vaccine formulation of claim 1, wherein the formulation comprises:
   a) G1, G2, G3, G4, and P1A rotavirus reassortants;
   b) 1.5 M sucrose;
   c) 465 mM adipic acid;
   d) 10 mM sodium phosphate; and
   e) 3 mM of a pharmaceutically acceptable salt of calcium.

11. The rotavirus vaccine formulation of claim 10, further comprising 0.01% w/v of polysorbate 80.

12. The rotavirus vaccine formulation of claim 1, wherein the formulation is thermally stable for at least 7 days at 37° C., at least 45 days at 25° C. and at least 2 years at 2-8° C.

13. A method of reducing the likelihood of rotavirus infection or for preventing or reducing the likelihood or severity rotavirus gastroenteritis in a child, comprising administering the formulation of claim 1 to the child orally.

14. The method of claim 13, wherein the child is an infant between the ages of 6 and 12 weeks of age.

15. The method of claim 13, further comprising the steps of: (a) waiting for a predetermined amount of time to pass; (b) administering an additional dose of the formulation to the child, and (c) optionally repeating steps (a) and (b) one or more times.

16. The method of claim 15, wherein the method comprises administering the rotavirus vaccine formulation to the child in a 3-dose series, wherein the child is 32 weeks of age or younger at the completion of the series.

17. The method of claim 13 wherein the rotavirus vaccine formulation is concomitantly administered to the child with a second vaccine selected from the group consisting of: diphtheria and tetanus toxoids and acellular pertussis (DTaP), inactivated poliovirus vaccine (IPV), *Haemophilus* influenza type b conjugate (Hib), hepatitis B vaccine, and pneumococcal conjugate vaccine and combination thereof.

* * * * *